US006955709B2

(12) United States Patent  
Magni

(10) Patent No.: US 6,955,709 B2  
(45) Date of Patent: Oct. 18, 2005

(54) METHOD AND DEVICE FOR VAPORIZATION INJECTION OF HIGH VOLUMES IN GAS CHROMATOGRAPHIC ANALYSIS

(75) Inventor: Paolo Magni, Iazno (IT)

(73) Assignee: Thermo Electron S.p.A., Rodano (IT)

( * ) Notice: Subject to any disclaimer, the term of this patent is extended or adjusted under 35 U.S.C. 154(b) by 23 days.

(21) Appl. No.: 10/450,165

(22) PCT Filed: Dec. 19, 2002

(86) PCT No.: PCT/IB02/05506

§ 371 (c)(1),
(2), (4) Date: Jul. 30, 2003

(87) PCT Pub. No.: WO03/060508

PCT Pub. Date: Jul. 24, 2003

(65) Prior Publication Data

US 2004/0050251 A1 Mar. 18, 2004
US 2004/0187682 A2 Mar. 18, 2004

(30) Foreign Application Priority Data

Dec. 28, 2001 (IT) .................................... MI2001A2840

(51) Int. Cl.$^7$ .............................................. B01D 15/08
(52) U.S. Cl. .............................. 95/87; 73/23.41; 95/89; 96/104; 96/105
(58) Field of Search ............................. 73/23.35, 23.41; 95/82, 83, 86–89; 96/101, 104–107

(56) References Cited

U.S. PATENT DOCUMENTS

| 3,513,636 | A | * | 5/1970 | Istvan et al. ................... 96/105 |
| 4,035,168 | A | * | 7/1977 | Jennings .................... 73/864.85 |
| 4,399,032 | A | * | 8/1983 | Mott ........................ 210/198.2 |
| 4,734,107 | A | | 3/1988 | Trestianu et al. |
| 5,227,059 | A | * | 7/1993 | Shepherd ................... 210/198.2 |
| 5,545,252 | A | * | 8/1996 | Hinshaw et al. ................ 95/15 |
| 5,759,234 | A | * | 6/1998 | Munari et al. .................. 95/14 |
| 5,779,765 | A | * | 7/1998 | Grob et al. ..................... 95/83 |
| 5,944,877 | A | | 8/1999 | O'Neil |
| 5,997,615 | A | * | 12/1999 | Luong et al. .................. 96/105 |
| 6,055,845 | A | * | 5/2000 | Gerstel et al. .............. 73/23.42 |
| 6,093,371 | A | * | 7/2000 | Wilson ......................... 422/89 |
| 6,131,440 | A | * | 10/2000 | Bertrand ..................... 73/23.39 |
| 6,134,945 | A | * | 10/2000 | Gerstel et al. .............. 73/23.42 |
| 6,180,410 | B1 | * | 1/2001 | Gerstel et al. ................. 436/54 |
| 6,223,584 | B1 | * | 5/2001 | Mustacich et al. .......... 73/23.41 |
| 6,257,047 | B1 | * | 7/2001 | Grob et al. ................. 73/23.42 |
| 6,389,879 | B1 | * | 5/2002 | Grob et al. ................. 73/23.42 |
| 6,565,634 | B1 | * | 5/2003 | van Egmond ................ 96/105 |
| 6,652,625 | B1 | * | 11/2003 | Tipler et al. .................... 95/82 |

FOREIGN PATENT DOCUMENTS

| EP | 0 753 739 A2 | 1/1997 |
| EP | 0 806 661 A1 | 11/1997 |
| EP | 0 959 351 A2 | 11/1999 |
| WO | WO 99/01759 | 1/1999 |

OTHER PUBLICATIONS

Grob et al., "Vaporising System for Large Volume Injection or On–Line Transfer Into Gas Chromatography: Classification, Critical Remarks and Suggestions," Journal of Chromatography A, Elsevier Science, NL, vol. 750, No. ½, Oct. 25, 1996, pp. 11–23; XP000637409.

Bosboom et al, "Large–Volume Injection in Capillary Gas Chromatography Using a Programmed–Temperature Vaporizing Injector in the On–Column or Solvent–Vent Injection Mode," Journal of Chromatography A, Elsevier Science, NL, vol. 724, No. ½, Feb. 16, 1996, pp. 384–391; XP000551419.

Grob, "Injection Techniques in Capillary GC," Analytical Chemistry. A, American Chemical Society, Columbus, US, vol. 66, No. 20, Oct. 15, 1994, pp. 1009a–1019a; XP002181891.

* cited by examiner

*Primary Examiner*—Robert H. Spitzer
(74) *Attorney, Agent, or Firm*—Nixon & Vanderhye P.C.

(57) ABSTRACT

This invention concerns a method and apparatus for vaporization injection of large volumes of liquid sample (substance to be analysed+solvent) introduced by a syringe needle into a heated vaporization chamber which is part of an injector coupled operatively to a device for gas chromatographic analysis. The sample is sent in the form of a liquid band traveling through the vaporization chamber at high speed until it reaches a stopping and vaporization device positioned adjacent to the inlet of a capillary to collect the vapors. In order to inject large volumes without modifying the vaporization chamber and without partial losses of the samples, the sample vapors, in splitless mode, are drawn up from the vaporization chamber into the capillary by virtue of the local action of volume contraction caused by recondensation of at least the solvent vapors in the capillary.

17 Claims, 3 Drawing Sheets

METHOD AND DEVICE FOR VAPORIZATION INJECTION OF HIGH VOLUMES IN GAS CHROMATOGRAPHIC ANALYSIS

This applications is the US national phase of international application PCT/IB02/05506, filed 19 Dec. 2002, which designated the US.

FIELD OF THE INVENTION

The present invention relates to a method and a device for vaporization injection of liquid samples in gas chromatographic analysis equipments. More specifically, the invention relates to a method and to a device specially adopted for vaporization injection of large volumes of liquid samples in a gas chromatograph using a split/splitless injector in splitless mode.

The term "large volumes of liquids" is intended as sample volumes (composed of the substance to be analysed and the related solvent) which are large or very large in relation to the gas chromatographic column and to the injection technique conventionally used.

BACKGROUND OF THE INVENTION

Therefore, columns with an internal diameter ranging from 0.25 mm to 0.53 mm and a vaporization chamber (liner) of an adequate volume, which allows the introduction of samples, in splitless mode, ranging from 1–3 $\mu$l, are normally used in gas chromatography. In these cases, without modifying the column or the vaporization chamber, the present invention allows the injection in splitless mode of samples greater than 5 $\mu$l and up to 50 $\mu$l and over.

Moreover, the use of "narrow bore" columns, with an internal diameter below 0.25 mm (typically from 0.10 to 0.18 mm), is becoming increasingly frequent. However, these columns, which have the advantage of a greater efficiency per unit of length, require the sample to be transferred from the vaporization chamber to the column in extremely brief times. This condition is exceedingly difficult to satisfy owing to the low flow rate at which these columns must work. This makes conventional splitless injection almost impossible and it is usually necessary to use a split injection, where only a small fraction of the sample is transferred to the column (usually only $1/50$–$1/100$ of 1 $\mu$l injected). The present invention makes it possible to transfer the sample in splitless mode also in chromatography with "narrow bore" columns. This aspect extends the range of application of the present invention, summed up here: 1) splitless injections of samples greater than 5 $\mu$l and up to 50 $\mu$l and over with traditional columns and 2) splitless injection of samples up to 1–5 $\mu$l and over with "narrow bore" columns.

Attempts have been made, in traditional chromatography, to increase the injectable volume of the samples, as current trends are aimed at an increase in the volumes to be injected, in order to be able to detect even very small quantities of the compound to be analysed and in a more straightforward manner; for this purpose techniques have been developed for discharging to the outside, without introducing them onto the gas chromatographic column, the majority of the solvent vapours which are formed first and are eliminated from the vaporization injection chamber. However, this often causes loss of the most volatile compounds which escape with the discharged solvent vapours.

The Italian patent application No. Ml 2000A001634 dated Jul. 19, 2000 and the corresponding European patent application no. 01114900.2, the content of which must be considered incorporated herein for reference, describe an injection device and a method of vaporization injection, in which the sample (formed of the substance to analyse and a related solvent) is introduced into the hot vaporization chamber at a high speed, so that it travels the entire length of the chamber in the form of a liquid bond. This band then hits a stopping and vaporization means, such as an obstacle, a packing or similar, at the bottom end of the chamber, where the liquid vaporizes to allow the introduction of the sample in the form of vapour onto the gas chromatographic column, the inlet to which is directly adjacent.

This technique makes it possible to avoid the problems as described in the cited application, of vaporization of the sample in the needle of the introduction syringe, and at the same time allows the length of the vaporization chamber to be extended to over 80 mm and hence samples of relatively large volume to be injected without problems of losses caused by overflow through the head of the chamber and/or the septum purging duct (see EP 699 303 for injection with overflow), and naturally without the loss of volatile substances which may occur if the solvent is eliminated before entering the column.

Nonetheless, although there is a considerable increase in the injectable volumes, from the 1–3 $\mu$l of conventional injectors to about 5–10 $\mu$l, these volumes are necessarily limited by the volume of the chamber, which cannot be increased as desired.

This being stated, the main object of the present invention is to provide a method and a device for vaporization injection in splitless mode of even larger sample volumes, without elimination of the solvent vapours towards the outside, that is by introducing the entire sample onto the gas chromatographic column and without phenomena of overflow or vaporization in the injection needle.

To attain this object it is necessary to perform a rapid injection of the sample, so as to create a liquid band of the same inside the heated vaporization chamber. This eliminates the drawbacks caused by the heating of the syringe needle. The problem of preventing the large volume of the vaporized sample, which cannot be contained in the chamber, from being dispersed, even only partly, in the head of the chamber and in septum purging duct (overflow) are still to be solved.

Therefore, the vapours must be sent to the gas chromatographic column at a substantially the same speed as the speed at which they form.

A solution to this problem was proposed, among others, in the publication of Watanabe and Hashimoto (Journal of High Resolution Chromatography Vol. 13 September 1990, 610–613) by using an injector for packed columns, without septum purging duct and without splitting, and injecting large volumes of sample (50 $\mu$l), at a low speed (about 5 $\mu$l/s) and with an increased speed of the carrier to deliver the vapours to a capillary kept cold during injection. The publications of Suzuki et al (Journal of AOAC International Vo. 77 No. 6, 1994. 1647-1641 and Journal of Chromatography A. 662 (1994) 139–146) also propose the use of a cold trap downstream of the injector, but again with a slow injection (2.5 $\mu$l/s) which produces the known problems of vaporization with loss of heavy products which remain in the needle and cause important errors in the analysis of the sample. The cold trap recondenses only the substances to be analysed, but not the solvent; which is discharged to the outside as vapour through a specific duct controlled by a valve.

Elimination of the solvent with the method described in the cited works also produces a loss of light components and, moreover, a deformation of the chromatography peaks, making a correct quantitative evaluation of the compounds with medium or high volatility impossible.

It must also be mentioned that Watanabe and Suzuki inject at controlled speed, which may be attained manually with extreme difficulty, and normally requires a special automatic sampler. Moreover, the appropriate speed must be optimized through experimentation.

SUMMARY OF THE INVENTION

The object of the invention is now perfectly attained by means of a method and device as defined in the attached claims. In practice, a pre-column which is not coated with stationary phase and maintained at least during, the injection at a temperature that causes recondensation of the solvent vapours, is provided between the injector and the gas-chromatographic column. This vapour recondensation produces a drop in pressure upstream which determines a collection (drawing up) of the vapours from the vaporization chamber. This allows large quantities of injected sample to be treated rapidly, as the vapours are collected from the chamber at substantially the some speed as they form, and therefore without these vapours expanding under pressure towards the top of the chamber and out of it, independently from the dimensions of the chamber.

In other words, while according to prior art in splitless mode vaporization injections and with the rapid introduction of the sample the volume of this was necessarily limited by the volume of the vaporization chamber, according to the invention this limitation is now overcome thanks to the collection of the solvent vapours substantially at the same speed as they form.

BRIEF DESCRIPTION OF THE DRAWINGS

The invention will be now described in greater depth with reference to the drawing FIGURES, wherein.

DESCRIPTION OF THE PREFERRED EMBODIMENT

Figure 1:
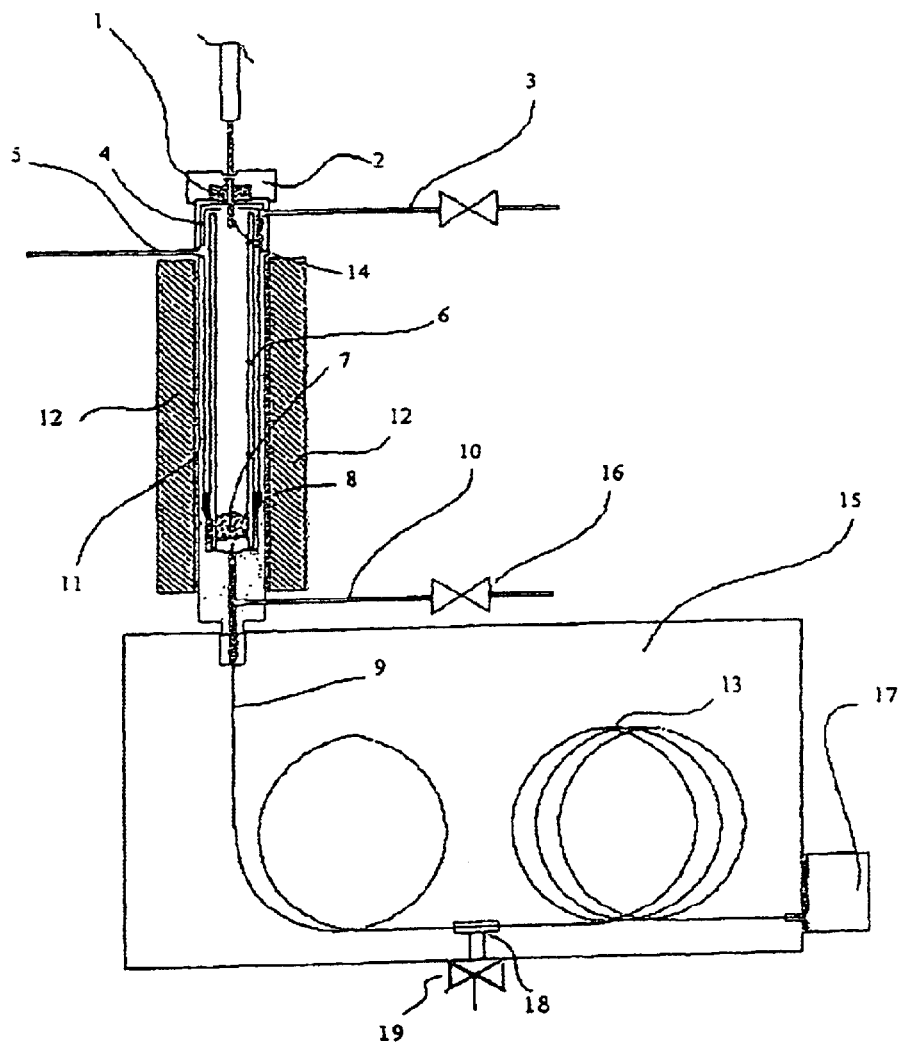
FIG. 1 is a schematic representation of a device for gas chromatographic analysis according to the invention.

With reference to FIG. 1, the body of an injector 11 houses a vaporization chamber 6 over which a septum 1 is positioned fixed to the injector by a sealing element 2.

The vaporization chamber 6 is heated preferably only in the lower portion thereof by well known heating elements 1.2, while the upper portion, closed by a cap 4, is preferably not heated.

The injector has a duct 5 for feeding the carrier gas and a duct 3 used to clean the septum by means of the carrier. The vaporization chamber is fixed to the injector body by means of a seal 8. The duct 10 schematically indicates a splitting line, with a related valve 16. The sample, taken using known techniques, is introduced into the chamber by means of a syringe, the needle 14 of which, in case smaller than conventional needles, perforates the septum 1 to reach a predetermined point in the chamber and inject the sample in liquid state as a "band" jet which travels the rest of the highly heated vaporization chamber at a speed that makes the transfer of heat and subsequent vaporization negligible. In any case, the liquid band is repelled by a sort of "buffer" effect determined by the vaporization of minimum quantities of solvent on the walls of the chamber, so that the band remains unaltered while travelling longitudinally through the chamber, and following the configuration of the same.

In particular, the sample is injected at or in the vicinity of the preferably unheated upper portion of the vaporization chamber, by a short needle 14 of a length which, for example, penetrates the chamber for a distance of no more than 30 mm. Alternatively, a longer needle may be introduced only partially.

For vaporization, the liquid sample is transferred to a stopping and vaporization means such as packing made of glass wool, deactivated fused silica or a material for packed columns, indicated in FIG. 1 with reference number 7. Alternatively, the sample is stopped on an obstacle or trapped between obstacles, as occurs in the case of the "laminar liner" supplied by the company Restek. The position of said packings or obstacles inside the chamber determines the central vaporization point of the sample and therefore they make it possible to prevent drops of liquid from entering the column 9 or passing directly into the splitting duct.

The operations to collect and introduce the sample onto the vaporization chamber 6 may be performed manually or using an automatic sampler.

It was found that an output speed of the sample from the needle, as normally obtained by manual injection, equivalent to about 10 m/second, is sufficient to transfer the liquid to the packing 7 without producing appreciable vaporization.

According to the invention of application MI 2000A001634, to allow high quantities of sample to be injected the capacity of the chamber is increased, also tending to eliminate the external "dead volumes", which allows enhancement of the "pressure pulse" effect obtained in a substantially automatic manner during the vaporization injection (auto pressure pulse).

With these methods, it is possible, for example, to introduce up to 10 $\mu$l of a sample dissolved in hexane.

In order to operate with larger quantities of sample with a vaporization chamber having the same or even smaller dimensions, the present invention provides a pre-column 9, composed of a capillary with no internal coating and of an adequate length (for example, 0.32 mm i.d.×5 m or 0.53 mm i.d.×3 m) positioned between the injector and the gas chromatographic column 13, inside an oven 15. Downstream of the column 13 a detector 17 is provided. The temperature of the oven and therefore of the pre-column 9 is maintained, at least for the entire duration of injection, at a value that determines recondensation of the solvent vapours entering the pre-column from the injection chamber. More specifically, this temperature must be below the dew point of the solvent vapour/carrier mix at the carrier pressure.

Recondensation of the solvent vapours in the pre-column 9 determines a great reduction in the volume and consequently a decrease in pressure in the upper zone of this pre-column, which "draws up" the solvent vapours in the pre-column at a speed substantially the some as the speed at which the vapours form in the chamber.

The dimensions of the pre-column 9 must allow for sufficient liquid retention capacity to contain almost all the sample.

The stopping and vaporization means 7 is preferably composed of deactivated glass wool positioned immediately over the inlet of the pre-column 9 to minimize the volume of carrier, present between the means 7 (glass wool) and the pre-column inlet, which must be introduced into the pre-column before the solvent vapours. The packing volume must be sufficient to retain the sample, while allowing the carrier to flow through. A volume of about 2–3 times the injected liquid volume is recommended.

As illustrated in the previously cited patent application by the same applicant, during rapid vaporization of the solvent a pressure pulse is created which helps to push the vapours into the column. In the present case, it is advisable for this pressure pulse to be as high as possible and therefore the injector is advantageously designed to minimize the "dead volumes", that is the volumes accessible around the vaporization chamber, moreover, it is also advisable to totally, or at least partially, close the purging outlet 3 of the septum during the entire injection. For the same reason, all filters (typically activated charcoal) between the vaporization chamber and the valve 16 for closure of splitting must be eliminated. If this filter (not shown) is required, it must be positioned downstream of the valve 16.

It must be noted that due to the pressure pulse and the violent vaporization of the solvent in the chamber, transfer of the vapours in the pre-column is hardly influenced at all by the carrier, the feed conditions of which (pressure and flow rate) may remain the same as those present during analysis.

It must also be noted that to obtain optimum transfer of the sample from the pre-column 9 to the gas chromatographic column 13 it is advisable to increase the temperature of the oven 15 only after evaporation of the solvent in the pre-column is terminated and the solvent has been removed from the pre-column by the carrier.

According to a possible alternative embodiment of the invention, a valve 19 can be placed at the junction 18 of the pre-column 9 to the column 13 to controllably discharge the solvent vapours or part of the solvent vapours before the introduction of the sample into the column 13.

Following the precepts of the invention, several 40 $\mu$l samples of n-alkanes in n-hexane in the quantity of 1 ng/ml each were analysed. The column was of the type SE52, 15 m in length, internal diameter 0.32 mm with a phase thickness of 0.15 $\mu$m, while the pre-column was formed of an empty (uncoated) capillary 2 m in length with an internal diameter of 0.53 mm. The oven temperature was maintained at 70° C. for the time of the injection and then increased for analysis at the speed of 20° C./min. up to 345° C., while the injector was maintained at 300° C. The splitless period was 0,80 min and during that time the purge duct of the septum was closed. Finally, helium was used as carrier at a flow rate of 2 ml/min.

Figure 2:
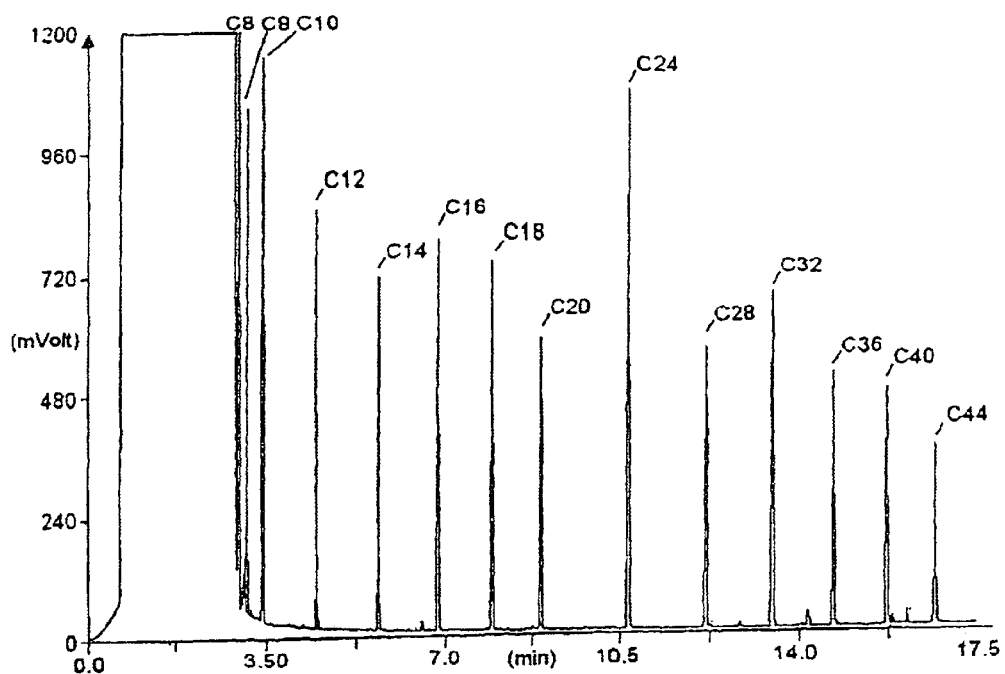
FIG. 2 is a chromatogram obtained by analyzing a sample of n-alkanes in n-hexane using the method and device according to the present invention.

The chromatogram of FIG. 2 was obtained and, on the basis of 10 analyses, the repeatability indicated in the table below was obtained.

TABLE

| Component | Retention times | | Peak areas | |
| --- | --- | --- | --- | --- |
| | mean | standard deviation | mean | RSD % |
| C10 | 2.40 | 0.0051 | 7.3E+07 | 0.20 |
| C12 | 3.66 | 0.0021 | 6.3E+07 | 0.28 |
| C14 | 4.96 | 0.0005 | 6.0E+07 | 0.23 |
| C16 | 6.15 | 0.0009 | 5.9E+07 | 0.22 |

TABLE-continued

| Component | Retention times | | Peak areas | |
| --- | --- | --- | --- | --- |
| | mean | standard deviation | mean | RSD % |
| C18 | 7.23 | 0.0010 | 7.2E+07 | 0.26 |
| C20 | 8.19 | 0.0011 | 6.3E+07 | 0.25 |
| C24 | 9.92 | 0.0009 | 1.0E+08 | 0.27 |
| C28 | 11.38 | 0.0007 | 6.4E+07 | 0.31 |
| C32 | 12.67 | 0.0012 | 6.1E+07 | 0.33 |
| C36 | 13.81 | 0.0012 | 5.8E+07 | 0.41 |
| C40 | 14.84 | 0.0007 | 4.5E+07 | 0.70 |
| C44 | 15.77 | 0.0012 | 3.7E+07 | 1.34 |

Figure 3:
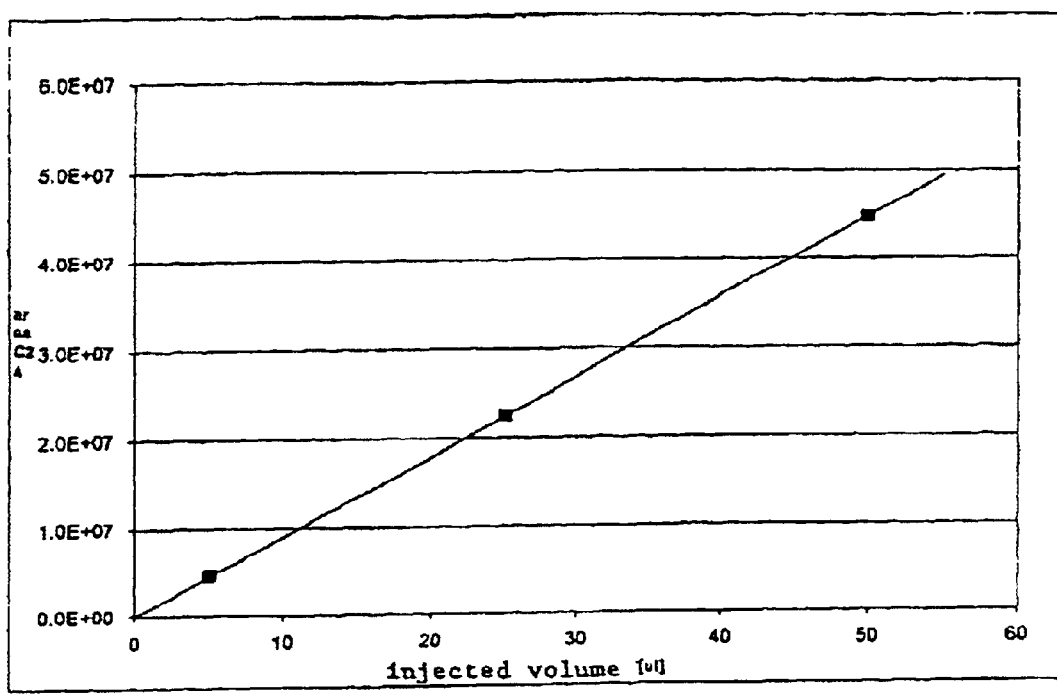
FIG. 3 is shows the linear correlation between the injected sample volume and the peak areas of the chromatogram.

Finally, on the basis of several analyses on different quantities of sample (from 5 to 50 $\mu$l) completely linear results were obtained, as shown in FIG. 3.

What is claimed is:

1. A method for vaporization injection of large volumes of liquid sample having a substance to be analysed and a solvent, said method comprising the steps of:
   introducing the liquid sample by means of a syringe needle into a permanently heated vaporization chamber which is part of an injector having an inlet for a carrier gas coupled operatively to a device for gas chromatographic analysis;
   causing the sample to travel through said vaporization chamber as a liquid band at a high speed;
   bringing the liquid band traveling at said high speed into contact with a stopping and vaporization means positioned adjacent an inlet of a capillary to thereby collect sample vapours therefrom, and wherein
   the method is practiced in a splitless mode and the capillary is in the form of a pre-column maintained at a sufficiently low temperature below a dew point of a mixture of the sample vapours and carrier gas at a carrier gas pressure which results in recondensation of at least the solvent vapours in the pre-column to cause the sample vapours to be drawn up from the vaporization chamber and into said pre-column.

2. A method as claimed in claim 1, wherein the pre-column has no stationary phase, and is maintained at said sufficiently low temperature at least during injection of the liquid sample.

3. A method as claimed in claim 2, wherein said pre-column has an internal surface sufficient to retain the recondensed sample.

4. A method as claimed in claim 2, which further comprises starting an increase in pre-column temperature after termination of evaporation of the solvent in said pre-column.

5. A method as claimed in claim 1, further comprising feeding the carrier during injection in flow and pressure conditions substantially equal to those foreseen during gas chromatographic analysis by the device coupled operatively to the inlet of the injector.

6. A method as claimed in claim 1, wherein the sample is sent through the injector as a liquid band, employing conditions that substantially avoid its vaporization in the needle.

7. A method as claimed in claim 6, wherein vaporization of the liquid band occurs at an end of the vaporization chamber opposite to an end at which the sample is introduced, immediately above the inlet of the pre-column.

8. A method as claimed in claim 1, wherein the injection sample has a volume greater than 5 $\mu$l.

9. A method as claimed in claim 1, wherein the capillary includes a narrow bore column gas chromatograph operated in the splitless mode.

10. A method as claimed in claim 9, wherein the injected sample has a volume greater than 0.5 µl.

11. A device for gas chromatographic analysis of samples having a substance to be analysed and a solvent, wherein sample injection is performed in splitless mode, said device comprising a vaporization type injector, an oven, a gas chromatographic column housed in the oven, and a detector, wherein the injector comprises, a heated chamber which includes a septum, said septum being capable of penetration by a syringe needle for fast injection of the sample in the form of a liquid band, a duct for feeding carrier gas into the injector, a capillary having an inlet for receiving sample vapours, a separation column coupled operatively to the capillary, and stopping and vaporization means positioned in the chamber for the stopping and vaporizing the liquid band of the sample adjacent to the inlet of the capillary to thereby collect the vapours and send the vapors to the separation column, wherein said capillary is in the form of a pre-column positioned between the injector and the separation column, and wherein said device comprises means for maintaining said pre-column, during sample injection, at a temperature below a dew point of a mixture of the sample vapours and carrier at a carrier pressure which results in recondensation of at least the solvent vapours in the pre-column to thereby responsively cause the sample vapours to be drawn up from the vaporization chamber.

12. A device as claimed in claim 11, wherein the vaporization chamber includes walls and heating means to heat the vaporization chamber, said heating means being positioned and operating so that a temperature profile on a longitudinal axis of the injector is such that a part in which the syringe needle penetrates is heated only slightly and a subsequent part is sufficiently hot to repel liquid from walls of the vaporization chamber due to formation of a vapour buffer.

13. A device as claimed in claim 11, wherein the stopping and vaporization means includes a packing having a volume at least double of a volume of the injected sample.

14. A device as claimed in claim 13, wherein the packing is made of glass wool, fused silica or similar deactivated materials.

15. A device as claimed in claim 11, wherein the stopping and vaporization means comprises obstacles.

16. A device as claimed in claim 11, further comprising a septum purging duct arranged relative to the septum so as to purge the septum by means of the carrier gas, and means to close or choke said septum purging duct.

17. A device as claimed in claim 11, wherein the pre-column has no stationary phase.

* * * * *

UNITED STATES PATENT AND TRADEMARK OFFICE
CERTIFICATE OF CORRECTION

PATENT NO. : 6,955,709 B2
DATED : October 18, 2005
INVENTOR(S) : Magni, P. et al.

It is certified that error appears in the above-identified patent and that said Letters Patent is hereby corrected as shown below:

Title page,
Item [75], Inventors, insert:
-- Paolo Magni, Izano, Italy
   Thomas Porzano, Vimercate (MI), Italy --.

Signed and Sealed this

Seventeenth Day of January, 2006

JON W. DUDAS
*Director of the United States Patent and Trademark Office*